United States Patent [19]

Khoobiar

[11] 4,169,099

[45] Sep. 25, 1979

[54] CATALYST AND PROCESS FOR PRODUCING ETHYLENE OXIDE

[75] Inventor: Sargis Khoobiar, Kinnelon, N.J.

[73] Assignee: Halcon Research and Development Corporation, New York, N.Y.

[21] Appl. No.: 909,327

[22] Filed: May 25, 1978

[51] Int. Cl.² ............... C07D 301/10; B01J 23/08; B01J 23/50
[52] U.S. Cl. ...................... 260/348.34; 252/463
[58] Field of Search ............... 252/463, 476; 260/348.34, 348.35

[56] References Cited

U.S. PATENT DOCUMENTS

| | | | |
|---|---|---|---|
| 3,758,418 | 9/1973 | Leonard et al. | 252/463 X |
| 4,045,369 | 8/1977 | Cantaluppi | 252/463 X |

FOREIGN PATENT DOCUMENTS

| | | | |
|---|---|---|---|
| 661089 | 4/1963 | Canada | 252/463 |
| 1451870 | 10/1976 | United Kingdom | 252/463 |

*Primary Examiner*—W. J. Shine
*Attorney, Agent, or Firm*—William C. Long; David Dick; Harold N. Wells

[57] ABSTRACT

In the oxidation of ethylene with molecular oxygen, improved selectivity to the production of ethylene oxide is obtained by employing a silver catalyst containing greater than zero and up to about 300 ppm by weight of thallium, based on the total catalyst.

8 Claims, 1 Drawing Figure

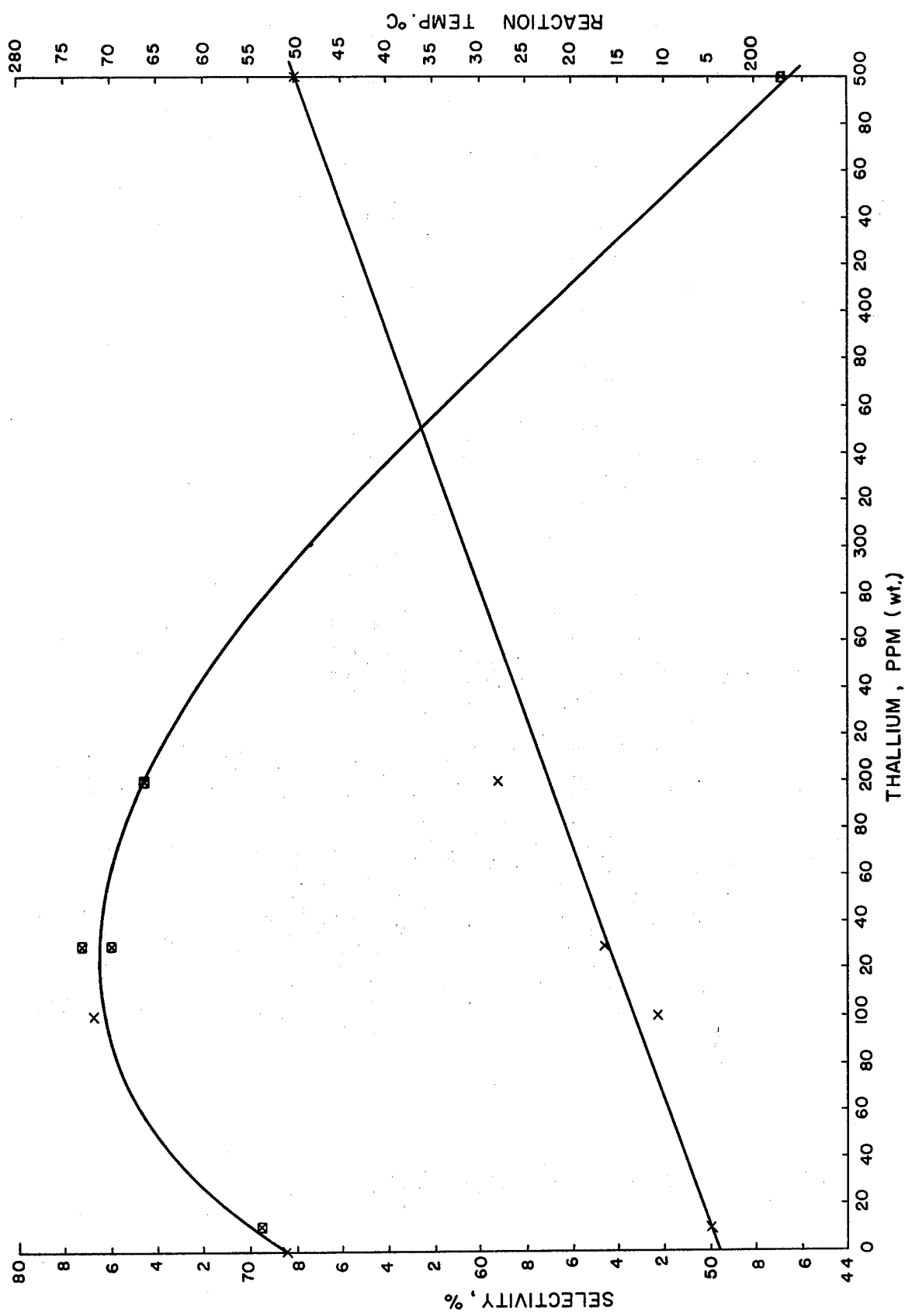

CATALYST AND PROCESS FOR PRODUCING ETHYLENE OXIDE

PRIOR ART

The invention relates to the oxidation of ethylene with molecular oxygen over a catalyst to produce ethylene oxide. Processes for oxidation of ethylene are generally known in the art. The catalyst used must promote the oxidation of ethylene to ethylene oxide, while minimizing the burning of the ethylene to carbon dioxide and water. Such a catalyst is said to have a high selectivity to the production of ethylene oxide. Typically, the catalyst used for oxidation of ethylene to ethylene oxide is a supported silver catalyst.

Generally, a supported silver catalyst in commercial operation will convert approximately 15 to 30% of the ethylene passing through the reactor, with a selectivity to ethylene oxide in the range of about 68% to about 72%. Since the conversion of ethylene is relatively small, a commercial plant will ordinarily recover the ethylene oxide from the reactor effluent and then recycle the unreacted gases back to the reactor until essentially all of the fresh ethylene has been converted to ethylene oxide or by-products.

It has been found that adding certain materials to the supported silver catalyst has the effect of improving selectivity of the catalyst to ethylene oxide. Recently, catalysts containing alkali metals, in particular, potassium, cesium, and rubidium have been employed commercially. Such catalysts are disclosed and claimed in U.S. Pat. No. 3,962,136 in which the alkali metals are used in quantities between $4 \times 10^{-5}$ and $8 \times 10^{-3}$ gram equivalent weight per kilogram of the total catalyst, and in U.S. Pat. No. 4,066,575, where the alkali metals are stated to be present in amounts from $4 \times 10^{-5}$ to $4 \times 10^{-3}$ gram atoms per kilogram of catalyst. It should be noted that the alkali metals are included in the silver catalyst in quite small amounts and, in fact, it is known that more than trace amounts of the alkali metals will degrade the performance of the catalyst.

Among the materials that have been disclosed as additives for supported silver catalysts is thallium. In U.S. Pat. No. 2,615,900, many materials, including thallium, are suggested for use in the form of halides to increase the yield of ethylene oxide. The amount of halides used may be substantial, according to the U.S. Pat. No. 2,615,900. A range of 0.01-50% by weight, based on metallic silver, is said to be effective.

Japanese publication No. 40769 (1972), of Teijin Ltd., discloses an ethylene oxide catalyst containing antimony oxide and a member of a group of compounds including thallium oxide.

Another and more general disclosure of thallium is found in U.S. Pat. No. 3,758,418 where thallium is mentioned along with many other metals, in connection with a method for producing catalysts characterized by having active metal particles of less than 1000 A, including those used for the manufacture of ethylene oxide. However, no reference is made to the use of thallium in connection with silver catalysts for ethylene oxide manufacture.

Another Japanese publication No. 50307 (1975) of Japan Catalytic Chemicals Industries, discloses silver catalysts containing tin and/or antimony and at least one of cesium, potassium, and thallium, and optionally barium, in small amounts relative to the principal constituent, silver. Thallium is evidently considered to be optional since it is shown to be present between zero and 0.1 atomic percent, based on the silver content.

Another recent U.S. Pat. No. 4,045,369, discloses an ethylene oxide catalyst containing a member of the group consisting of barium, strontium, and calcium, along with indium as additives to silver. The patentee indicates that, while thallium is considered to be a poison, it may be tolerated in amounts up to 1% based on the silver content.

It has now been found that thallium can be used to provide an improved ethylene oxide catalyst having higher selectivity than a catalyst without thallium, but that this effect is obtained only over a relatively narrow range of compositions, as will be discussed hereinafter.

SUMMARY OF THE INVENTION

In one aspect, the invention comprises a process for the production of ethylene oxide by oxidation of ethylene with molecular oxygen over a supported silver catalyst containing an optimal quantity of thallium namely, greater than zero and up to about 300 ppm by weight, preferably 10 to 270 ppm by weight, and most preferably 70 to 180 ppm by weight, based on the total catalyst. Within the stated ranges of composition, adding thallium results in a catalyst having superior selectivity to ethylene oxide compared to catalysts containing lesser or greater amounts of thallium. In amounts greater than about 300 ppm by weight, thallium reduces the selectivity of the catalyst to ethylene oxide compared to the same catalyst containing no thallium.

In another respect, the invention comprises a supported silver catalyst for the production of ethylene oxide by oxidation of ethylene with molecular oxygen which contains up to about 300 ppm by weight of thallium, preferably 10 to 270 ppm by weight, and most preferably 70 to 180 ppm by weight. The support preferably will have a surface area less than about 1 m²/gm and an apparent porosity in the range of 40-60%. Preferably the catalyst will contain 3 to 25% by weight of silver deposited on the support.

BRIEF DESCRIPTION OF THE DRAWINGS

The sole FIGURE shows the effect of varying amounts of thallium on the selectivity of supported silver ethylene oxide catalyst.

DESCRIPTION OF THE PREFERRED EMBODIMENTS

Catalyst Composition

Supported silver catalysts for oxidation of ethylene with molecular oxygen to ethylene oxide are widely known in the art. The silver is normally supported on an inert material having relatively low surface area, i.e., less than about 10 square meters per gram, preferably less than 1.0 square meters per gram. The support should have an apparent porosity of at least 30%, and preferably in the range of about 40 to 60%. Surface area is the value measured by the BET technique (the Brunauer, Emmet, and Teller method, J. Am. Chem. Soc., 60, 309-16 (1938)) and the apparent porosity is the value measured by the mercury absorption method (Drake & Ritter, Ind. Eng. Chem. Anal Ed, 17,787 (1945)). While a number of supports may be used, including alumina, silica, mixtures of silica and alumina, silica-alumina, and silicon carbide, preferably silica-alumina is used.

Typical supports are the low surface, alpha-alumina-containing materials manufactured by the Norton Company. One such material, designated SA-5252, is used as a support in the examples given hereinafter. It has the following nominal composition: 93.1 wt % alumina, 5.6 wt % silica, apparent porosity 51-57% (with 10% of the pores having a diameter less than 1 micron, 40% of the pores in the range of 1-10 microns, 34% of the pores in the range of 10-100 microns, and 6% greater than 100 microns). Surface area is between 0.2-0.5 square meters per gram and pore volume is 0.31 cc per gram.

Since the oxidation reaction is highly exothermic, the catalyst particles are commonly disposed within relatively small diameter tubes from which the heat of reaction can be readily dissipated. Consequently, the particles must be within a fairly narrow size range in order to obtain suitable performance in such reactors. The supports are commonly formed into regular shapes, i.e. spheres, rings, etc., and generally are in the range of 4.76 mm to 7.94 mm (3/16" to 5/16") equivalent diameter.

The finished catalyst ordinarily will contain an amount of silver in the range of about 3-25% by weight of the total catalyst, preferably about 8-15% by weight. Greater amounts of silver are effective, but unduly expensive, while lesser amounts are undesirable since the useful life of the catalyst is shortened.

Other materials known to have a promotional effect may be included in the catalyst, such as members of Groups Ia and IIa of the Periodic Table. Barium is one such promoting material, which if used is present in amounts which are typically in the range of 10-5000 ppm by weight as metal, and preferably in the range of 100-500 ppm by weight, based on the total catalyst.

It has been found that when thallium is included in ethylene oxide catalysts, the amount used must be limited to very small quantities, generally greater than zero and up to about 300 ppm by weight, based on the total catalyst. Improved selectivity to ethylene oxide is found particularly when amounts of thallium between 10 and 270 ppm by weight of the total catalyst are used. Most preferably, the catalyst will contain an amount of thallium in the range of about 70 to 180 ppm by weight based on the total catalyst.

Catalyst Preparation

A number of methods of preparing ethylene oxide catalysts have been disclosed in the art. One recent patent which discusses important considerations in preparing such catalysts is U.S. Pat. No. 4,066,575. The preferred method of catalyst preparation to be discussed here is not believed to be critical to obtaining the benefits of minor amounts of thallium, and other methods known to the art may be also employed.

Preferably, the support particles previously discussed are impregnated by soaking them in a silver solution containing the sufficient quantities of silver and selected promoters, if any, plus thallium, until the desired quantity of catalytic materials has been deposited. The amount of silver used in impregnating solutions will vary, but typical solutions may contain from 5-50 wt % silver in the form of a silver compound or complex. The silver may be in the form of any number of organic compounds such as silver acetate, benzoate, oxalate, malonate, succinate, glutarate, and maleate. In U.S. Pat. No. 4,066,575 is a typical example of an impregnating solution, and which contains 55 to 73 wt % silver lactate, 15 to 45 wt % lactic acid, 0.05 to 0.3 wt % barium acetate, 0 to 0.5 wt % hydrogen peroxide (an oxidizer for silver), and from 0-20% water.

Thallium is included in the solution as a soluble thallium compound, which can be decomposed during the usual catalyst activation procedures. In general, the wide variety of compounds discussed with respect to silver also may be useful as thallium compounds. In particular, thallium acetate or hydroxide have been found to be convenient, although others such as thallium chloride or nitrate may be used.

As will be understood by those skilled in the art, the concentration of the metals in the impregnating solution will affect the amount of metals deposited, as also will the nature of the support and the time and temperature at which the impregnation is carried out. These variables will be adjusted to provide the desired amount of metals on the support.

Although aqueous solutions of salts of silver and promoters are preferred, organic metal complexes, non-aqueous solutions of inorganic metal compounds, and molten metal salts may also be employed, as discussed in U.S. Pat. No. 4,066,575.

The catalyst support particles are immersed in a solution for about 1-60 minutes at temperatures from 30°-120° C., although the period of immersion and the temperature may be adjusted in order to obtain the desired amount of absorption of catalytic materials into the support particles. Typically, immersion for 5-15 minutes at a temperature of under about 100° C. is preferred. A single immersion ordinarily will be sufficient to deposit the desired amount of silver under the conditions described above. However, multiple immersions, with or without intermediate drying, may be employed.

It should be noted that it is not considered critical, as is disclosed in some of the prior art, to carry out separate impregnations for the silver and the promoters although such step-wise preparations could be carried out. It has been found satisfactory to simply include the thallium compounds in the silver-containing impregnating solution in order to co-deposit silver and thallium on the support.

After completion of the impregnation of the particles, they are removed from the solution and then dried at moderate temperatures ranging from ambient to about 175° C., preferably from about 75° to 150° C., for a period of time sufficient to completely remove the moisture. Typically, drying is carried out for 8-10 hours or more in air.

After the particles have been dried, it is an important part of the preparation process to activate the particles by heating to decompose the silver compound or complex and to reduce the resulting silver oxide in order to produce an active catalyst. The promoter metal compounds, such as thallium acetate, are also decomposed during the activation process. It is common practice to heat the particles gradually in the presence of air to temperatures in the range of 200°-300° C. or more and to retain that temperature until the activation is complete. After the catalysts have been activated, they may be used for the oxidation of ethylene to ethylene oxide.

Process of Use

The oxidation of ethylene to ethylene oxide by molecular oxygen over a silver support catalyst usually takes place in the range of about 150°-400° C. Typical commercial operations will be carried out in the range of 200°-300° C. It may be noted that lower temperatures are generally preferred in order to avoid excessive combustion of ethylene to carbon dioxide and water, which in effect lowers the selectivity of the process to production of the desired ethylene oxide. The reaction is carried out at a pressure in the range of about 0.5–35 kg/cm$^2$ gauge. The feed mixture typically will contain in the range of about 0.5–20 mol % ethylene, 3–15 mol % oxygen, and the remainder inerts such as carbon dioxide, nitrogen, methane, ethane, argon, and the like. The inert gases have an important effect on the performance of the catalyst system, in particular, by assisting in the removal of the substantial heat of reaction.

Although the selectivity of the reaction under the conditions described and with the preferred catalyst typically will be in the range of about 74 to 78%, the amount of ethylene contained in the feed which is actually converted, will be relatively small, say about 15 to 30%. Consequently, the reactor effluent is treated to remove ethylene oxide and the remaining unreacted gases are returned to the reactor.

It has been found that the catalyst of the invention, containing an optimum quantity of thallium produces a significantly improved selectivity to ethylene oxide compared to the same catalyst without thallium. The beneficial effect on selectivity of adding thallium is, however, limited to a relatively narrow range, beyond which the effect of thallium is to reduce activity, as will be seen in the following examples and the accompanying FIGURE.

EXAMPLE I

To 95 parts of an 88 wt % aqueous lactic acid solution is added 50 parts of silver oxide and 1 part of 30 wt % hydrogen peroxide solution, and the mixture stirred until a clear yellow solution of silver lactate is obtained, containing 32.5 wt % silver (as metal).

A barium acetate solution containing 0.537 wt % barium (as metal) is prepared by mixing 1 part of barium acetate and 99 parts of water. A portion of the solution (20 parts) is added to the silver lactate solution.

Ten parts of a 25 wt % aqueous thallium hydroxide solution are dissolved in 490 parts of water to form a solution containing 0.5 wt % thallium hydroxide. A portion of the solution (9 parts) is added to the silver lactate-barium acetate solution.

The silver lactate-barium acetate solution containing thallium hydroxide is heated to a temperature of about 95° C. and 69 parts of Norton SA-5252 silica-alumina support in the form of 4.76 mm spheres are immersed in the solution. After 45 minutes, the impregnated catalyst particles are removed and drained free of the non-absorbed solution.

The drained particles are then placed in an oven and heated gradually to a temperature of 100° C. to dry the particles over a period of 10 hours in air. Then the temperature is raised from the drying temperature of 100° C. to 250° C. in order to decompose the organic compounds present and to deposit silver, barium and thallium oxides over a 2 hour period. Thereafter, the particles are heated to 350° C. over about 1 hour and held at that temperature for 1 hour to calcine the catalyst in air. After cooling, the catalyst is ready for use and is found to contain 15 wt % silver, 0.033 wt % barium, and 130 ppm weight thallium, based on the finished catalyst.

EXAMPLE II

To 95 parts of an 88 wt % lactic acid solution is added 50 parts of silver oxide and 1 part of 30 wt % hydrogen peroxide solution, and the mixture stirred until a clear yellow solution of silver lactate is obtained, containing 32.5 wt % silver (as metal).

Ten parts of a 25 wt % aqueous thallium hydroxide solution are dissolved in 490 parts of water to form a solution containing 0.5 wt % thallium hydroxide. A portion of the solution (9 parts) is added to the silver lactate solution.

The silver lactate solution containing thallium acetate is heated to a temperature of about 95° C. and 69 parts of Norton SA-5252 silica-alumina support in the form of 4.76 mm spheres are immersed in the solution. After 45 minutes, the impregnated catalyst particles are removed and drained free of the nonabsorbed solution.

The drained particles are placed in an oven and heated gradually to a temperature of 100° C. to dry the particles over a period of 10 hours in air. Then, the temperature is raised from the drying temperature of 100° C. to 250° C. in order to decompose the organic compounds present and to deposit silver over a 2 hour period. Thereafter, the particles are heated to 350° C. over about 1 hour and held at that temperature for 1 hour to calcine the catalyst in air. After cooling, the catalyst is ready for use and is found to contain 15 wt % silver, and 130 ppm weight thallium, based on the finished catalyst.

EXAMPLE III

A series of activated catalysts is prepared according to the method of Example II and the amount of thallium varied to cover the range of up to 500 ppm (wt) thallium based on the finished catalyst. The catalysts containing varying amounts of thallium are tested in a single tube reactor (1.386 mm i.d.) by exposing 65 grams of the catalyst to 3300 M$^3$ (N.T.P.)/hr-M$^3$ cat of a feed gas containing 5 mol % ethylene, 6.1 mol % oxygen, and 4.5 mol % CO$_2$ (balance nitrogen), at a pressure of 21.1 kg/cm$^2$ gauge and at the temperature required to produce 1 mol % ethylene oxide at the outlet of the reactor (200° to 250° C.). A small amount of ethylene dichloride, about 0.25 ppm by volume, is added as a reaction modifier. The reactor temperature is adjusted by a thermostatically controlled system employing a commercial heat transfer oil which circulates through a jacket surrounding the reactor tube. The selectivity to ethylene oxide of the oxidation reaction is determined and the following results obtained.

TABLE I

| Thallium ppm, wt. | Selectivity to EO % (@ 1% EO made) | Average Reactor Temperature, °C. |
|---|---|---|
| 10 | 69.7 | 205 |
| 100 | 76.7 | 211 |
| 130 | 76–77.2 (2 runs) | 217 |
| 200 | 74.6 | 228 |
| 500 | 46.7 (@ 0.45% EO) | 250 |

The data represent average values for runs carried out for periods between 53 and 156 hours, but it should be noted that once the desired amount of ethylene oxide is being produced, the performance of the catalyst remains relatively constant and selectivity values are averaged to minimize the effect of analytical variations. The selectivity at 500 ppm thallium is reported at an outlet composition of only 0.45% ethylene oxide rather than at 1% ethylene oxide since 1% could not be achieved with such an amount of thallium present.

The reactor temperature is also reported as an indirect measure of the activity of the catalysts. It will be observed that with no thallium present, the catalyst can be operated at a relatively low temperature while producing the desired 1% ethylene oxide in the gases exiting the reaction tube and having a selectivity of about 68%. As thallium is added, the temperature required to provide the desired amount of ethylene oxide increases and this would ordinarily be expected to reduce selectivity to ethylene oxide. However, the selectivity actually increases as thallium is added until a maximum improvement is observed between about 70 to about 180 ppm. Thereafter, the selectivity decreases, until above about 300 ppm the catalyst has no better selectivity for ethylene oxide than a catalyst containing no thallium. The addition of thallium to provide an improvement in selectivity of about 8% would have considerable value in commercial production of ethylene oxide.

An optimized catalyst would preferably contain about 70 ppm to about 180 ppm by weight thallium based on the total catalyst. Considered more broadly, and as shown by the FIGURE, the catalyst should contain greater than zero and up to 300 ppm thallium, generally at least about 10 ppm thallium and a maximum of about 270 ppm thallium in order to obtain a notably improved selectivity to ethylene oxide. Indeed, when the amount of thallium exceeds about 300 ppm, the performance of the catalyst is poorer than catalyst containing no thallium.

The foregoing description of the preferred embodiments of the invention is for information and should not be considered to limit the scope of the invention, which is defined by the claims which follow.

What is claimed is:

1. A supported silver catalyst for production of ethylene oxide by oxidation of ethylene with molecular oxygen wherein the improvement consists essentially of increasing the selectivity of said catalyst for production of ethylene oxide by including greater than zero and up to 300 ppm by weight of thallium based on said catalyst.

2. The catalyst of claim 1 wherein said catalyst includes between 10 and 270 ppm by weight of thallium.

3. The catalyst of claim 1 wherein said catalyst includes between 70 and 180 ppm by weight of thallium.

4. A supported silver catalyst for production of ethylene oxide by oxidation of ethylene with molecular oxygen consisting essentially of a support having a surface area less than 1 $m^2/gm$ and an apparent porosity in the range of 40–60% and 3 to 25 wt % silver as metal deposited on said support, wherein the improvement consists essentially of including greater than zero and up to 300 ppm by weight of thallium as metal deposited on said support, and thereby increasing the selectivity of said catalyst for production of ethylene oxide.

5. The catalyst of claim 4 wherein said silver and said thallium are co-deposited on said support from a solution containing compounds of both of said silver and thallium, followed by drying and calcining of said support and silver and thallium deposited thereon.

6. The catalyst of claim 4 wherein said catalyst includes between 10 and 270 ppm by weight thallium.

7. The catalyst of claim 4 wherein said catalyst includes between 70 and 180 ppm by weight thallium.

8. A process for production of ethylene oxide by oxidation of ethylene with molecular oxygen carried out over the catalyst of claim 1.